(12) United States Patent
Theil

(10) Patent No.: US 6,325,977 B1
(45) Date of Patent: Dec. 4, 2001

(54) OPTICAL DETECTION SYSTEM FOR THE DETECTION OF ORGANIC MOLECULES

(75) Inventor: Jeremy A Theil, Mountain View, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/484,330

(22) Filed: Jan. 18, 2000

(51) Int. Cl.[7] .................... G01N 21/00; G01N 21/29; G01N 27/00; G01N 15/06; G01N 25/18

(52) U.S. Cl. ................ 422/82.05; 422/68.1; 422/82.1; 422/82.3; 422/82.5; 436/6; 436/94; 436/149

(58) Field of Search .................. 422/68.1, 82.01, 422/82.05, 82.03; 436/149, 94, 6

(56) References Cited

U.S. PATENT DOCUMENTS

| | | | |
|---|---|---|---|
| 4,926,231 | * 5/1990 | Hwang et al. | 357/30 |
| 5,846,708 | 12/1998 | Hollis | 435/6 |
| 5,936,261 | 8/1999 | Ma et al. | 257/59 |
| 5,965,452 | * 10/1999 | Kovacs | 436/149 |

FOREIGN PATENT DOCUMENTS

| | | |
|---|---|---|
| 0895082A2 | * 2/1999 | (EP) . |
| WO 99/27140 | * 6/1999 | (WO) . |

OTHER PUBLICATIONS

Blanchard et al, "Sequence to array: probing the genome's secrets; DNA probe construction for usein the human genome project", Nature Biotechnology, 1996, 14(13), p. 1649.*

McGall et al, "Synthesis of high–density oligonculeotide arrays for hybridization–based sequence analysis", Book of Abstracts, American Chemical Society, Apr. 13–17, 1997, ORGN–367.*

* cited by examiner

*Primary Examiner*—Michael Borin

(57) ABSTRACT

An optical detection system. The optical detection system includes an integrated circuit, photosensors, a passivation layer formed above the photosensors, and test sites formed on the passivation layer. The test sites include test probes of organic material that are able to bind with target organic molecules. The combination of the test probes and target organic molecules can be activated such that light is given off from the test sites in proportion to the concentration of target molecules. Light given off from the test sites is detected by the photosensors that are present below the passivation layer. The photosensors generate electronic signals in proportion to the amount of light received from the test sites. The electronic signals are then transmitted from the photosensors to the integrated circuit for signal processing. Signal processing within the integrated circuit can enhance the quality of the electronic signals generated by the photosensors. The integrated circuit and photosensors can be fabricated utilizing known fabrication techniques, such as CMOS.

31 Claims, 3 Drawing Sheets

OPTICAL DETECTION SYSTEM FOR THE DETECTION OF ORGANIC MOLECULES

FIELD OF THE INVENTION

The invention relates generally to the detection of organic molecules, and more particularly to the detection of organic molecules, such as DNA, utilizing an optical sensor array.

BACKGROUND

Organic molecules, such as DNA and RNA, can be analyzed utilizing genetic chips that include a matrix of test sites. A single genetic chip may include 1,000 to 500,000 individual test sites. The test sites are individually activated and responses are detected utilizing various activation and detection techniques. One technique for analyzing organic molecules involves combining the molecules with optically active receptors. The optically active receptors are then activated and light emitted from each test site is individually detected and quantified.

One known system for detecting light at a test site includes a charged coupled device (CCD) that is formed in close proximity to each test site. For example, an array of test sites can be formed over a CCD array such that each pixel of the CCD array corresponds to an individual test site. While this optical detection technique works well, there are disadvantages to utilizing CCD arrays.

Although CCD arrays have been widely utilized as image sensors, CCD arrays require specialized processes and equipment for fabrication. CCD arrays are also difficult to integrate with digital and analog circuitry that is designed around standard complementary metal oxide semiconductor (CMOS) technology. In addition, CCD arrays dissipate large amounts of power and may suffer from image smearing problems.

An alternative to a CCD array is active pixel sensor array. Active pixel sensor arrays can be fabricated utilizing CMOS technology and, therefore, can be easily integrated with digital and analog signal processing circuitry. Further, CMOS circuits dissipate smaller amounts of power compared to CCDs.

In view of the disadvantages of CCD arrays and the availability of active pixel sensors, what is needed is a system for optically detecting organic molecules that utilizes active pixel sensors.

SUMMARY OF THE INVENTION

The invention includes an integrated circuit, photosensors integrated with the integrated circuit, a passivation layer formed above the photosensors, and test sites formed on the passivation layer. The test sites may include test probes of organic material that are able to bind with target organic molecules. The combination of the test probes and target organic molecules can be activated such that light is given off from the test sites in proportion to the concentration of target molecules. Light given off from the test sites is detected by the photosensors that are present below the passivation layer. The photosensors generate electronic signals in proportion to the amount of light received from the test sites. The electronic signals are then transmitted from the photosensors to the integrated circuit for signal processing. Signal processing within the integrated circuit can enhance the quality of the electronic signals generated by the photosensors.

A first embodiment of an optical detection system includes an integrated circuit, an insulation layer, photodiodes, a transparent conductive layer, a passivation layer, and test sites.

The integrated circuit is electrically connected to the photodiodes and may include sensing circuits, signal processing circuits, or other circuits that support signal detection and readout. Techniques utilized to fabricate the integrated circuit may include CMOS, BiCMOS, or Bipolar.

The insulation layer separates the photodiodes from the integrated circuit. The insulation layer is patterned to provide contact holes (generally one per pixel) between the photodiodes and the integrated circuit.

The photodiodes, also referred to as active pixel sensors, generate electrical signals having amplitudes that are related to the intensity of the light that is received by the photodiodes. The photodiodes may include PIN, NIP, PN, or Schottky diodes.

The transparent conductive layer acts as the front electrode for the photodiodes. The transparent conductive layer is deposited as a continuous film and is a common electrode for all of the pixels.

The passivation layer is a transparent layer that provides an electrical barrier between the test sites and the transparent conductive layer. In an embodiment, the passivation layer is formed of silicon dioxide.

The test sites are preferably located directly above photodiodes such that each test site corresponds to a photodiode. That is, a test site and a photodiode are located in close proximity to each other and have a one to one correspondence.

The test probes include organic molecule receptors that are capable of binding to known molecular structures. The known molecular structures that bind to the receptors are referred to as targets. The targets may include biopolymers, such as polynucleotides, polypeptides, DNA, RNA, cells, or antibodies. The test probes are formed at the test sites utilizing techniques such as inkjet based writing, electrochemical based writing, and photolithography.

The targets, also referred to as the sample, are typically marked with tags that give off light when activated. For example, the tags may include compounds that fluoresce when activated. The targets are introduced to the test probes so that compatible test probes and targets can bind together. After the test probes and targets have bound together, the test sites are activated. Techniques for activating test sites in order to generate light include chemiluminescence, electroluminescence, and electrochemiluminescence. The particular activation technique is not critical to the invention and therefore is not described further. If an activated test site includes a tag bound to the test probe, then the test site generates light that is detected by the corresponding photodetector. The amount of light generated at each test site gives an indication of the presence and concentration of the target.

A method for forming a detection system includes fabricating an integrated circuit that includes photosensors. A passivation layer is deposited above the photosensors. Test sites are formed above the passivation layer. Additionally, test probes of organic material are bound to the passivation layer.

Preferably, test sites and photosensors are arranged in a manner that maximizes the collection efficiency of the light generated from each photosensor while minimizing interference from neighboring test sites. Because the test sites are located directly above the photosensors, there are no external optical paths between the test sites and the photosensors. The short optical paths between the test sites and the photosensors result in high light collection efficiency.

Other aspects and advantages of the present invention will become apparent from the following detailed description, taken in conjunction with the accompanying drawings, illustrating by way of example the principles of the invention.

DETAILED DESCRIPTION

Figure 1:
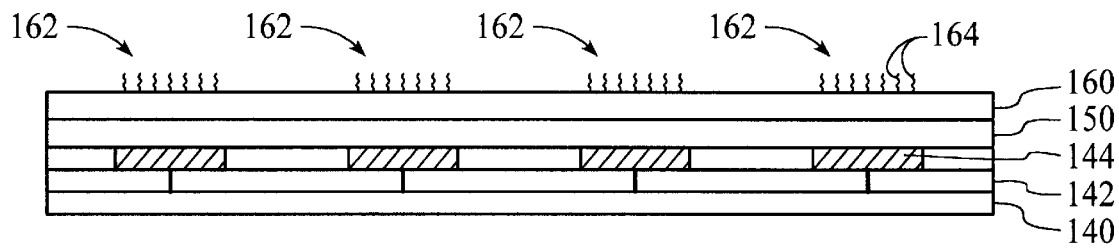
FIG. 1 shows an embodiment of an optical detection system that includes test sites and photodiodes that are formed above an integrated circuit, in accordance with the invention.

As shown in the drawings for purposes of illustration, the invention is embodied in a detection system that includes an integrated circuit (IC), active pixel sensors, a passivation layer, and test sites.

FIG. 1 shows a first embodiment of an optical detection system that includes active pixel sensors that are elevated above an IC. The optical detection system includes, from bottom to top, an IC 140, an insulation layer 142, photodiodes 144, a transparent conductive layer 150, a passivation layer 160, and test sites 162.

The IC 140 is electrically connected to the photodiodes 144 and may include sensing circuits, signal processing circuits, or other circuits that support signal detection and readout. Techniques utilized to fabricate the IC may include CMOS, BiCMOS, or Bipolar. In an embodiment, the top surface of the IC is planarized before subsequent layers are deposited.

The insulation layer 142 separates the photodiodes 144 from the IC 140. The insulation layer is patterned to provide contact holes (generally one per pixel) between the photodiodes and the IC. The contact holes are filled with conductive material to form vias. The vias provide the electrical connection between the photodiodes and the IC.

The photodiodes 144, also referred to as active pixel sensors, generate electrical signals having amplitudes that are proportional to the intensity of the light that is received by the photodiodes. Although shown in simplified form, the photodiodes may include electrodes, inner metal sections, an I-layer, and a doped layer that are formed to create PIN, NIP, or Schottky diodes. Other types of photosensors may also be utilized. Although only four photodiodes are shown, it should be understood that an optical detection system may include an array of photodiodes.

The transparent conductive layer 150 acts as the front electrode for the photodiodes 144. The transparent conductive layer is deposited as a continuous film and is a common electrode for all of the pixels.

The passivation layer 160 is a transparent layer that provides an electrical barrier between the test sites 162 and the transparent conductive layer 150. In an embodiment, the passivation layer is formed of silicon dioxide. In an embodiment, the silicon dioxide layer is approximately 5,000 angstroms thick.

The test sites 162 are preferably located directly above photodiodes 144 (pixels) such that each test site corresponds to a photodiode. That is, a test site and a photodiode are located in close proximity to each other and have a one to one correspondence. Preferably, test sites and photodiodes are arranged in a manner that maximizes the collection efficiency of the light generated from each photodiode while minimizing interference from neighboring test sites. Although not shown in FIG. 1, the test sites may include depressions or other features in the passivation layer which enhance the ability of test probes to bind to the test sites. Because the test sites are located directly above the active pixel sensors, there are no external optical paths between the test sites and the sensors. The short optical paths between the test sites and the sensors result in high light collection efficiency.

The test probes 164 include organic molecule receptors that are capable of binding to known molecular structures. The known molecular structures that bind to the receptors are referred to as targets. The targets may include biopolymers, such as polynucleotides, polypeptides, DNA, RNA, cells, or antibodies, although this list is not exhaustive. The test probes are formed at the test sites utilizing techniques such as inkjet based writing, electrochemical based writing, and photolithography.

The targets, also referred to as the sample, are typically marked with tags that give off light when activated. For example, the tags may include compounds that fluoresce when activated. The targets are introduced to the test probes so that compatible test probes and targets can bind together. After the test probes and targets have bound together, the test sites are activated. Techniques for activating test sites in order to generate light include chemiluminescence, electroluminescence, and electrochemiluminescence. The particular activation technique is not critical to the invention and therefore is not described further. If an activated test site includes a tag bound to the test probe, then the test site generates light that is detected by the corresponding photodetector. The amount of light generated at each test site gives an indication of the presence and concentration of the target.

In operation, the test probes 164 are exposed to target material utilizing known techniques. The test probes are allowed to bind with the target material to form combined molecules. The test sites 162 are then activated and light generated from each test site is individually detected by corresponding photodiodes 144. The photodiodes generate electronic signals that are related to the intensity of the light that is generated from the corresponding related test sites. The electrical signals generated by the photodiodes are then transmitted to the IC 140 for further signal processing. Providing an IC on the same chip as the test sites and photodiodes allows for more effective signal processing of the electrical signals generated by the photodiodes.

Figure 2:
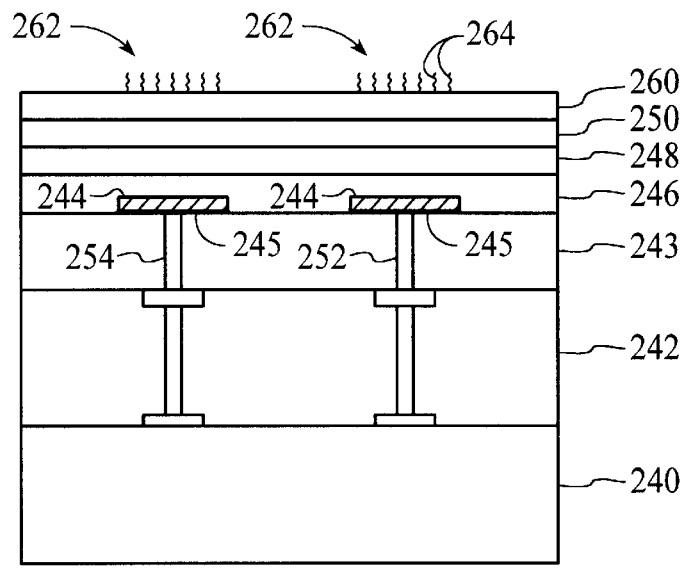
FIG. 2 shows an embodiment of an optical detection system that includes test sites and active pixel sensors that are formed above an integrated circuit, in accordance with the invention.

FIG. 2 shows a second embodiment of an optical detection system. The second embodiment includes more detail regarding the photodiode structure and the interconnection structure between the IC and the photodiodes. The structure of FIG. 2 is related to U.S. patent application Ser. No. 09/174,717, entitled "AN ELEVATED PIN DIODE ACTIVE PIXEL SENSOR WHICH INCLUDES A PAT- TERNED DOPED SEMICONDUCTOR ELECTRODE", which is assigned to the assignee of the current application and incorporated by reference herewith. As shown in FIG. 2, an interconnection structure 242 is formed adjacent to the IC 240. A pixel interconnect structure 243 is formed adjacent to the interconnection structure. Pixel electrodes 244 and an inner metal section 245 are formed adjacent to the pixel interconnect structure. Each pixel sensor of an array of pixel sensors includes an individual patterned pixel electrode and an inner metal section. An I-layer 246 is formed adjacent to the pixel electrodes. An upper doped layer, such as a P-layer 248, is formed adjacent to the I-layer. A transparent conductive layer 250 is formed adjacent to the P-layer. A passivation layer 260 is formed adjacent to the transparent conductor layer. Test sites 262 and test probes 264 are formed on top of the passivation layer. Although only two pixels and test sites are shown, it should be understood that an optical detection system may include a single pixel and a single test site or an array of pixels and test sites.

The pixel electrode 244 of a first pixel sensor is electrically connected to the IC 240 through a first conductive via 252. The pixel electrode of a second pixel sensor is electrically connected to the IC through a second conductive via 254.

The pixel sensors conduct charge when the pixel sensors receive light. The IC 240 generally includes sense circuits and signal processing circuits. The sense circuits quantify how much charge the pixel sensors have generated. The amount of charge conducted represents the intensity of light received by the pixel sensors. Generally, the IC can be formed with CMOS technology. Typically, the interconnection structure 242 is a standard CMOS interconnection structure. The structure and methods of forming this interconnection structure are well known in the field of electronic integrated circuit fabrication. The interconnection structure can be a subtractive metal structure, or a single or dual damascene structure.

The pixel interconnect structure 243 provides reliability and structural advantages to the elevated pixel sensor structure. The pixel interconnect structure allows for the formation of thin pixel electrodes 244 because the pixel electrodes are formed over silicon rather than a metal pad located on the interconnection structure 242. The pixel interconnect structure electrically connects the pixel electrodes to the interconnection structure. The pixel interconnect structure is typically formed from a dielectric film, for example, polyimide, silicon oxide or a silicon nitride.

The vias 252, 254 pass through the pixel interconnect structure 243 and electrically connect the pixel electrodes 244 to the IC 240. Typically, the conductive vias are formed from tungsten utilizing a chemical vapor deposition (CVD) process. Tungsten is generally used during fabrication because tungsten can fill high aspect ratio holes. That is, tungsten can be used to form narrow and relatively long interconnections. Other materials, which can be used to form the conductive vias include copper, aluminum or any other electrically conductive material.

There are several structural advantages to having the pixel interconnect structure 243 between the pixel electrodes 244 and the IC 240. This structure allows the interconnection circuitry to be tightly packed. First of all, lateral space is conserved because the vias 252, 254 are located directly underneath the pixel electrodes. Secondly, the structure allows for the formation of vias having a minimal diameter. As described above, CVD processes are generally the best method of forming the vias and a tungsten CVD process allows for the formation of small diameter vias. However, the temperatures required to form tungsten vias with a CVD process are greater than many of the materials (amorphous silicon for example) used to form the pixel electrodes can withstand. By forming the pixel interconnect structure over the IC, and the pixel electrodes over the pixel interconnect structure, the vias can be formed before the pixel electrodes, and therefore, the pixel electrodes are not subjected to the high temperatures required for the formation of the vias.

The inner metal section 245 preferably includes a thin conductive material. The inner metal section may be formed, for example, from a degenerately doped semiconductor, aluminum, titanium, titanium nitride, copper or tungsten. The inner metal section should be thin (approximately 500 angstroms). The inner metal section should be smooth enough that any surface roughness is substantially less than the thickness of the pixel electrode 244 formed over the inner metal section. To satisfy the smoothness requirement, polishing of the inner metal section may be required.

The inner metal section 245 can be optional. However, the inner metal section has a lower resistance than the materials used to form the pixel electrodes 244. Therefore, the inner metal section provides better current collection capability.

The pixel electrodes 244 are generally formed from a patterned doped semiconductor. The patterned doped semiconductor can be an N-layer of amorphous silicon. The pixel electrodes must be thick enough, and doped heavily enough that the pixel electrodes do not fully deplete when biased during operation. The pixel electrodes are typically doped with phosphorous.

The pixel electrodes are typically deposited using plasma enhanced chemical vapor deposition (PECVD). The PECVD may be performed with a phosphorous containing gas. For example, the phosphorous gas can be $PH_3$. A silicon containing gas is included when forming amorphous silicon pixel electrodes. To create the pixel electrodes, an N-layer of amorphous silicon is first deposited. Then a predetermined pixel electrode pattern (patterned doped semiconductor layer) is formed through a wet or dry etch of the deposited pixel electrode material. Because the pixel electrode material is etched after being deposited, the vacuum conditions in which the semiconductor substrate and partially formed active pixel sensor are subject to is broken. That is, the semiconductor substrate and partially formed active pixel sensor must be removed from vacuum conditions in order for the pixel electrode material to be etched. Generally, it is believed that breaking the vacuum conditions will result in impurities being introduced into the active pixel sensor formation process. However, for the purposes of this invention, breaking the vacuum conditions appear not to be a problem.

A patterned N-layer of amorphous silicon is typically used when forming PIN diode active pixel sensors. However, the diode active pixel sensors can include a NIP sensor configuration. When utilizing a NIP diode, the pixel electrodes 244 are formed from a patterned P-layer, and the P-layer 248 of FIG. 2 is replaced with an N-layer.

The I-layer 246 is generally formed from a hydrogenated amorphous silicon. The I-layer can be deposited using a PECVD or reactive sputtering process. The PECVD process must include a silicon containing gas. The deposition should be at a low enough temperature that hydrogen is retained within the film. The I-layer is approximately one micron thick.

The upper doped layer, such as P-layer 248, is generally formed from amorphous silicon. Typically, the P-layer is doped with boron. The P-layer can be deposited using PECVD. The PECVD may be performed with a boron containing gas. The boron containing gas can be $B_2H_6$. A silicon containing gas is included when forming an amorphous silicon P-layer. The P-layer thickness must generally be controlled to ensure that the P-layer does not absorb too much short wavelength (blue) light.

Another embodiment of the invention does not include a P-layer. The P-layer can be eliminated with proper selection of the composition of material within the transparent conductor 250, and proper selection of the doping levels of the pixel electrodes 244.

As previously described, the pixel electrodes 244, the I-layer 246 and the upper doped layer, for example P-layer 248, are generally formed from amorphous silicon. However, the pixel electrodes, the I-layer and the upper doped layer can also be formed from amorphous carbon, amorphous silicon carbide, amorphous germanium, or amorphous silicon-germanium. It should be understood that this list is not exhaustive.

The transparent conductive layer 250 allows for biasing of the P-layer 248 of the pixel sensors. Light must pass through the transparent conductive layer that is received by the pixel sensors. Generally, the transparent conductive layer is formed from an indium tin oxide. However, the transparent conductive layer can also be formed from titanium nitride, zinc oxide, thin silicide, or certain types of transition metal nitrides or oxides.

Both the selection of the type of material to be used within the transparent conductive layer 250, and the determination of the desired thickness of the transparent conductive layer, are based upon minimizing the optical reflection of light received by the pixel sensor. Minimization of the reflection of light received by the pixel sensor helps to optimize the amount of light detected by the pixel sensor. The transparent conductive layer can be deposited by a sputtering process. Deposition through sputtering is well known in the art of integrated circuit fabrication.

Another embodiment of the detection system includes Schottky diode sensors. Schottky diode sensors include several different configurations. A first Schottky diode configuration includes the electrodes 244 being formed from a conductive metal. This configuration also includes the I-layer 246 and the P-layer 248. A second Schottky diode configuration includes the electrodes being formed from a conductive metal and the P-layer being replaced with a transparent conductive layer or a transparent silicide. A third Schottky diode configuration includes the electrodes being formed from an N-layer, and the P-layer being replaced with a transparent conductive layer. The transparent conductive layer of the third configuration must exhibit a proper work function. Conductive metals which may be used for the Schottky configurations include chrome, platinum, aluminum and titanium.

As described above with reference to FIG. 1, the passivation layer 260 is a transparent layer that provides an electrical barrier between the test sites 262 and the transparent conductive layer 250. In an embodiment, the passivation layer is formed of silicon dioxide. In an embodiment, the silicon dioxide layer is approximately 5,000 angstroms thick.

The test sites 262 are preferably located directly above active pixel sensors (pixels) such that each test site corresponds to a pixel. Preferably, test sites and active pixel sensors are arranged in a manner that maximizes the collection efficiency of light generated from each pixel while minimizing interference from neighboring test sites. Although not shown in FIG. 2, the test sites may include depressions or other features in the passivation layer 260 which enhance the ability of the test probes to bind to the test sites.

The test probes 262 include organic molecule receptors that are capable of binding to targets. The targets may include biopolymers, such as polynucleotides, polypeptides, DNA, RNA, cells, or antibodies. The test probes are formed at the test sites utilizing techniques such as inkjet based writing, electrochemical based writing, and photolithography.

The targets, also referred to as the sample, are typically marked with tags that give off light when activated. For example, the tags may include compounds that fluoresce when activated. The targets are introduced to the test probes so that compatible test probes and targets can bind together. After the test probes and targets have bound together, the test sites are activated. Techniques for activating test sites in order to generate light include chemiluminescence, electroluminescence, and electrochemiluminescence. The particular activation technique is not critical to the invention and therefore is not described further. If an activated test site includes a tag bound to the test probe, then the test site generates light that is detected by the corresponding photodetector. The amount of light generated at each test site gives an indication of the presence and concentration of the target.

Figure 3:
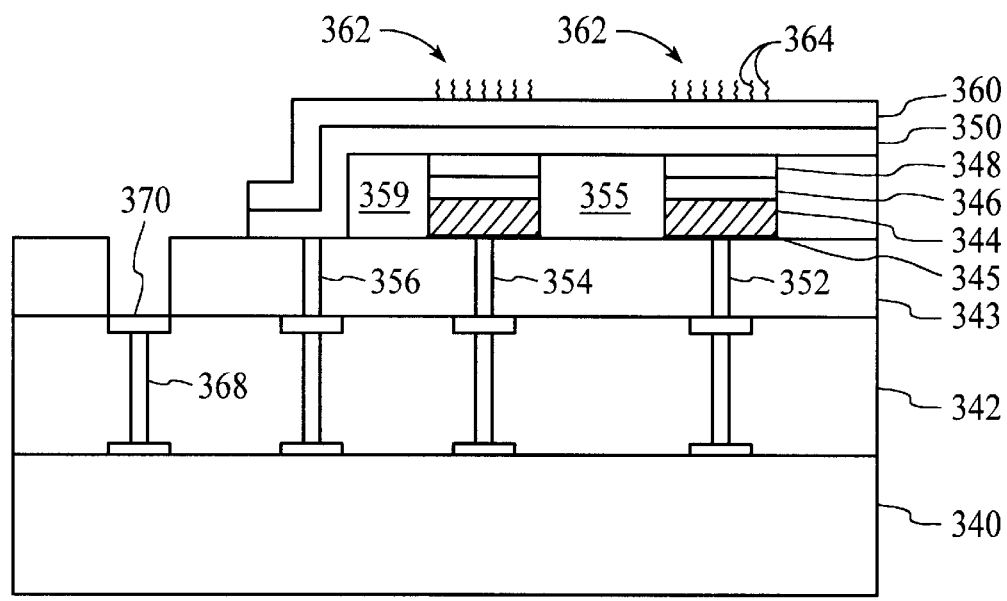
FIG. 3 shows an embodiment of an optical detection system that includes test sites and active pixel sensors that are formed above an integrated circuit, in accordance with the invention.

FIG. 3 shows a third embodiment of an optical detection system. The third embodiment includes more detail regarding the photodiode structure and the interconnect structure between the IC and the photodiodes. The structure of FIG. 3 is related to U.S. Pat. No. 5,936,261, entitled "ELEVATED IMAGE SENSOR ARRAY WHICH INCLUDES ISOLATION BETWEEN THE IMAGE SENSORS AND A UNIQUE INTERCONNECTION", which is assigned to the assignee of the current application and incorporated by reference herewith. The structure of FIG. 3 is similar to the structure of FIG. 2 except that the structure of FIG. 3 includes insulating regions 355 and an edge insulating region 359 that insulate the photodiode structures from each other and from the edge of the array. The structure of FIG. 3 also shows that the transparent conductor layer 350 is electrically connected to the IC 340 through a third conductive via 356. A fourth conductive via 368 electrically connects a contact pad 370 to the IC. Although only two pixels and test sites are shown, it should be understood that an optical detection system may include a single pixel and a single test site or an array of pixels and test sites.

As described above with reference to FIG. 1, the passivation layer 360 is a transparent layer that provides an electrical barrier between the test sites 362 and the transparent conductive layer 350. In an embodiment, the passivation layer is formed of silicon dioxide and is approximately 5,000 angstroms thick.

The test sites 362 are preferably located directly above active pixel sensors (pixels) such that each test site corresponds to a pixel or pixels. Preferably, test sites and photodiodes are arranged in a manner that maximizes the collection efficiency of each photodiode while minimizing interference from neighboring test sites.

The test probes 364 include organic molecule receptors that are capable of binding to target materials. The target materials may include biopolymers, such as polynucleotides, DNA, RNA, cells, or antibodies. The test probes are formed at the test sites 362 utilizing techniques such as inkjet based writing, electrochemical based writing, and photolithography.

The test probes 364 typically include tags that give off a known response depending on whether or not a probe and a target have combined. For example, a probe may include a fluorescent tag that gives off less light when the probe has combined with a target. Techniques for activating test sites 362 in order to generate light include chemiluminescence, electroluminescence, and electrochemiluminescence.

The targets, also referred to as the sample, are typically marked with tags that give off light when activated. For example, the tags may include compounds that fluoresce when activated. The targets are introduced to the test probes so that compatible test probes and targets can bind together. After the test probes and targets have bound together, the test sites are activated. Techniques for activating test sites in order to generate light include chemiluminescence, electroluminescence, and electrochemiluminescence. The particular activation technique is not critical to the invention and therefore is not described further. If an activated test site includes a tag bound to the test probe, then the test site generates light that is detected by the corresponding photodetector. The amount of light generated at each test site gives an indication of the presence and concentration of the target.

Figure 4:
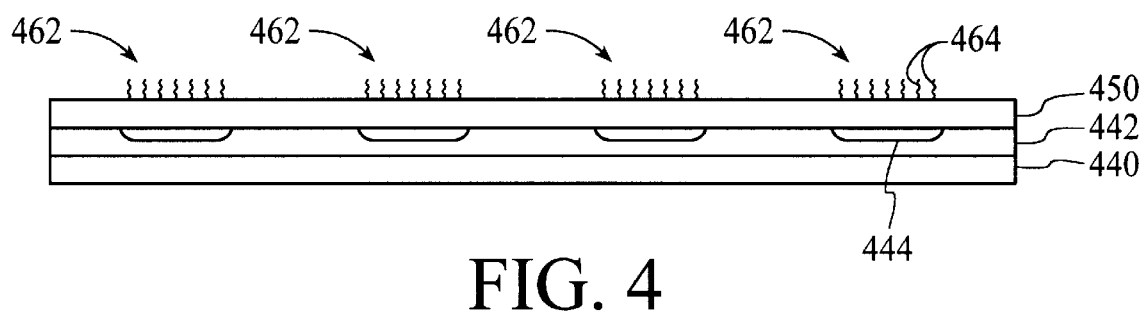
FIG. 4 shows an embodiment of an optical detection system that includes test sites formed above an integrated circuit that includes integrated photosensors, in accordance with the invention.

FIG. 4 shows a fourth embodiment of an optical detection system that includes transistors and photodetectors integrated into the same substrate. The optical detection system of FIG. 4 includes an IC 440, four photosensors, a passivation layer 450, and test sites 462. As shown in FIG. 4, the photosensors are photodiodes that include n-wells 444 that are formed in a p-substrate 442 utilizing techniques that are well known in the field of photosensor fabrication. The passivation layer is formed over the photosensors. The passivation layer is a transparent layer that provides an electrical barrier between the test sites and the transparent conductive layer. In an embodiment, the passivation layer is formed of silicon dioxide. In an embodiment, the silicon dioxide layer is approximately 5,000 angstroms thick. Although only four photodiodes and test sites are shown, it should be understood that an optical detection system may include a single photodiode and a single test site or an array of photodiodes and test sites.

The test sites 462 are preferably located directly above the photodiodes such that each test site corresponds to a photodiode. That is, a test site and a photodiode are located in close proximity to each other and have a one to one correspondence. Preferably, test sites and photodiodes are arranged in a manner that maximizes the collection efficiency of light generated from each photodiode while minimizing interference from neighboring test sites.

The test probes 464 include organic molecule receptors that are capable of binding to targets. The targets may include biopolymers, such as polynucleotides, polypeptides, DNA, RNA, cells, or antibodies. The test probes are formed at the test sites utilizing techniques such as inkjet based writing, electrochemical based writing, and photolithography.

The targets, also referred to as the sample, are typically marked with tags that give off light when activated. For example, the tags may include compounds that fluoresce when activated. The targets are introduced to the test probes so that compatible test probes and targets can bind together. After the test probes and targets have bound together, the test sites are activated. Techniques for activating test sites in order to generate light include chemiluminescence, electroluminescence, and electrochemiluminescence. The particular activation technique is not critical to the invention and therefore is not described further. If an activated test site includes a tag bound to the test probe, then the test site generates light that is detected by the corresponding photodetector. The amount of light generated at each test site gives an indication of the presence and concentration of the targets.

Figure 5:
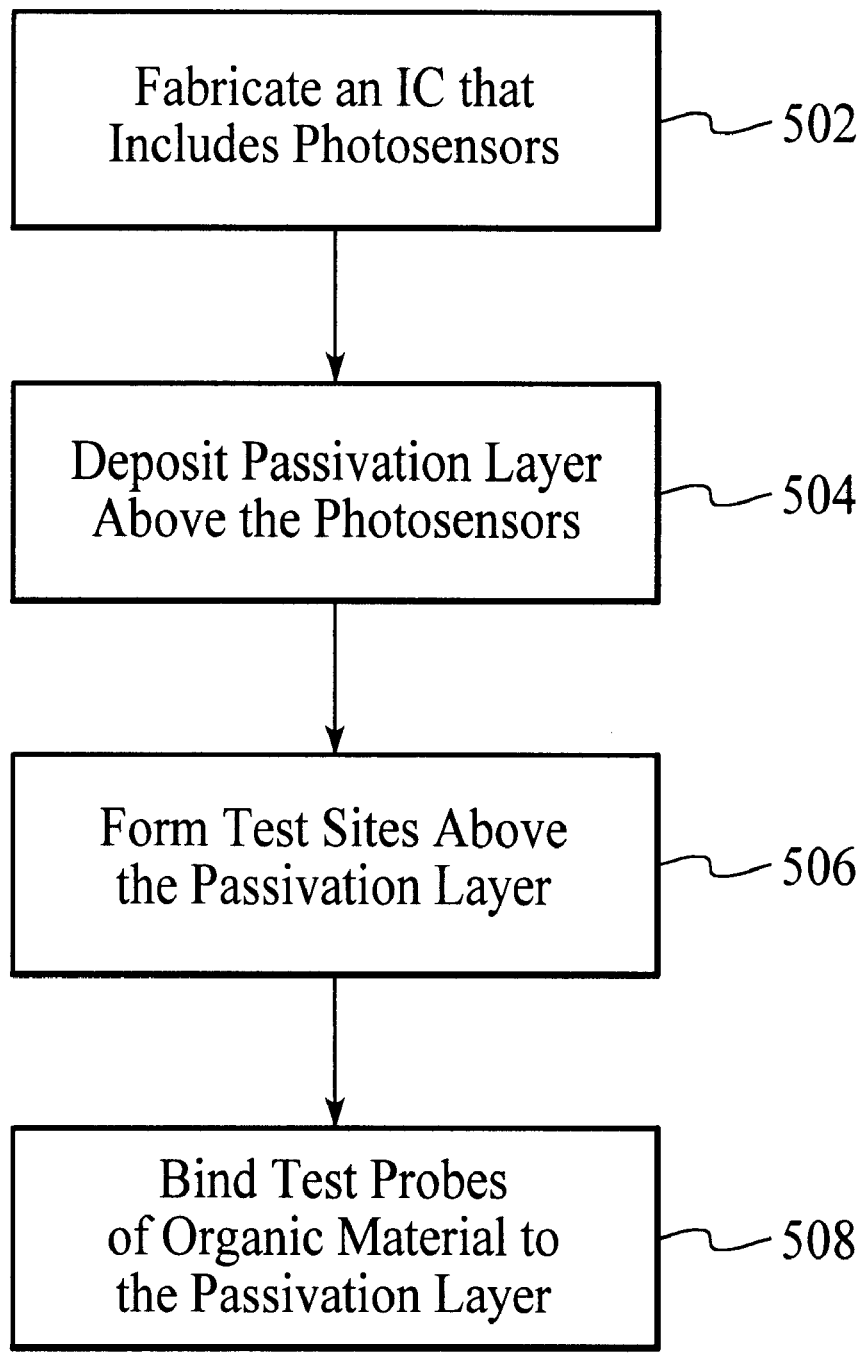
FIG. 5 is a process flow diagram of a method for forming a detection system that includes test sites formed above an integrated circuit that includes integrated photosensors, in accordance with the invention.

FIG. 5 represents a preferred method for forming a detection system similar to the detection system described with reference to FIGS. 1–4. In a first step 502, an IC that includes photosensors is fabricated. IC In a next step 504, a passivation layer is deposited above the photosensors. In a next step 506, test sites are formed above the passivation layer. In an additional step 508, test probes of organic material are bound to the passivation layer.

What is claimed is:

1. A detection system comprising:
   an integrated circuit;
   an interconnect structure formed above said integrated circuit;
   a plurality of photosensors formed above said interconnect structure;
   a passivation layer formed above said plurality of photosensors; and
   means for receiving organic material adjacent to said passivation layer;
   said passivation layer providing an electrical barrier between said photosensors and said means for receiving organic material.

2. The detection system of claim 1 wherein said means for receiving includes test sites.

3. The detection system of claim 2 wherein said test sites include features formed in said passivation layer.

4. The detection system of claim 2 wherein said test sites include test probes of organic material.

5. The detection system of claim 4 wherein said test sites are located directly above said photosensors.

6. The detection system of claim 1 wherein said photosensors are photodiodes.

7. The detection system of claim 6 wherein said photodiodes are PIN photodiodes.

8. The detection system of claim 1 wherein said integrated circuit comprises CMOS.

9. The detection system of claim 1 wherein said integrated circuit includes active circuits that process electrical signals generated by said photosensors in response to said photosensors receiving light.

10. The detection system of claim 1 wherein each of said photosensors comprises:
    a pixel electrode;
    an I-layer formed above said pixel electrode; and
    a transparent electrode formed above said I-layer.

11. The detection system of claim 10 further including a P-layer formed between said I-layer and said transparent electrode.

12. The detection system of claim 1 wherein each of said photosensors comprises:
    a pixel electrode;
    a separate I-layer section formed above said pixel electrode;
    said detection system further comprising:
      an insulating material between each photosensor; and
      a transparent electrode formed over said photosensors.

13. The detection system of claim 12 wherein each photosensor further includes a separate P-layer section formed between said I-layer section and said transparent electrode.

14. The detection system of claim 1 wherein said interconnect structure electrically interconnects said photosensors to said integrated circuit.

15. A method for forming an organic material detection system comprising the steps of:

fabricating an integrated circuit;

forming an interconnect structure above said integrated circuit;

depositing a doped semiconductor layer above said interconnect structure;

etching said doped semiconductor layer to form pixel electrodes;

depositing an I-layer above said pixel electrodes;

depositing a transparent conductive layer above said I-layer to form photosensors;

depositing a passivation layer above said transparent conductive layer; and forming test sites above said passivation layer.

16. The method of claim 15 wherein said step of fabricating said integrated circuit includes a step of forming an elevated array of amorphous silicon photodiodes.

17. The method of claim 15 wherein said step of forming test sites above said passivation layer includes a step of binding test probes of organic material to said passivation layer.

18. The method of claim 17 wherein said integrated circuit and said photosensors include CMOS devices.

19. The method of claim 17 wherein said step of binding test probes includes a step of writing test probes utilizing inkjet writing.

20. The method of claim 17 wherein said step of binding test probes includes a step of writing test probes utilizing electrochemical writing.

21. The method of claim 17 wherein said step of binding test probes includes a step of writing test probes utilizing photolithography.

22. The method of claim 17 wherein said step of fabricating said integrated circuit includes planarizing said integrated circuit before said photosensors are fabricated.

23. The method of claim 15 wherein said step of fabricating said integrated circuit includes steps of forming said photosensors above said integrated circuit and electrically connecting each of said photosensors to said integrated circuit through said interconnect structure.

24. A detection system comprising:

an integrated circuit containing signal processing circuits;

an interconnect structure formed above said integrated circuit;

a plurality of photodiodes formed above said interconnect structure, wherein each one of said photodiodes is electrically connected to said integrated circuit by a unique connection that runs through said interconnect structure;

a passivation layer formed above said plurality of photodiodes; and test sites formed above said passivation layer and located directly above said photodiodes, said test sites having test probes of organic material that are bound to said passivation layer.

25. The detection system of claim 24 wherein said integrated circuit and said photodiodes include CMOS.

26. The detection system of claim 24 wherein said photodiodes are an array of elevated amorphous silicon photodiodes.

27. The detection system of claim 24 wherein each of said photodiodes comprises:

a pixel electrode;

an I-layer formed above said pixel electrode; and a transparent electrode formed adjacent to said I-layer.

28. The detection system of claim 27 further including a P-layer formed above said I-layer.

29. The detection system of claim 24 wherein each of said photodiodes comprises:

a pixel electrode;

a separate I-layer section formed above said pixel electrode;

the detection system further comprising:

an insulating material between each photodiode; and a transparent electrode formed over said photodiodes.

30. The detection system of claim 29 wherein each photodiode further includes a separate P-layer section formed above said I-layer section.

31. The detection system of claim 24 wherein said test sites include features formed in said passivation layer.

* * * * *